United States Patent [19]

Rothman

[11] 4,275,208
[45] Jun. 23, 1981

[54] PREPARATION OF 1-PIPERIDINE-CARBODITHIOIC ACID PIPERIDINIUM SALT

[75] Inventor: Leonard A. Rothman, Great Neck, N.Y.

[73] Assignee: E. I. Du Pont de Nemours and Company, Wilmington, Del.

[21] Appl. No.: 144,298

[22] Filed: Apr. 28, 1980

[51] Int. Cl.$^3$ .......................................... C07D 401/12
[52] U.S. Cl. ..................................... 546/189; 546/245
[58] Field of Search ................................ 546/245, 189

[56] References Cited

U.S. PATENT DOCUMENTS 2,153,043  4/1939  Harman ................................. 546/189

FOREIGN PATENT DOCUMENTS 316009 11/1919 Fed. Rep. of Germany ........... 546/189

Primary Examiner—Robert T. Bond

[57] ABSTRACT

1-Piperidine-carbodithioic acid piperidinium salt is prepared from piperidine and carbon bisulfide mixed in water, optionally containing a surfactant, and heated.

6 Claims, No Drawings

PREPARATION OF 1-PIPERIDINE-CARBODITHIOIC ACID PIPERIDINIUM SALT

DESCRIPTION

1. Technical Field

This invention relates to the preparation of 1-piperidine-carbodithioic acid piperidinium salt in the presence of water optionally containing surfactant.

2. Background Art

1-Piperidine-carbodithioic acid piperidinium salt is known to the chemical industry and widely used as an accelerator for natural rubber and as a peptizer for neoprene. U.S. Pat. No. 2,153,043 discloses the preparation by reacting piperidine with carbon bisulfide in the presence of an aliphatic ketone, preferably acetone, which is then filtered, washed with the ketone and dried. The ketone is recovered by distillation for reuse.

3. Summary of the Invention

A new process for preparation of 1-piperidine-carbodithioic acid piperidinium salt has been found which eliminates the use of flammable solvents, i.e., the ketone. According to the present invention there is provided a process for preparing 1-piperidine-carbodithioic acid piperidinium salt wherein carbon bisulfide is added to piperidine in water and the solution is then heated above the boiling point of carbon bisulfide, e.g., 52°–56° C. The reaction mixture is cooled, filtered, washed with water and the product dried. There is also provided a process for preparing 1-piperidine-carbodithioic acid piperidinium salt wherein carbon bisulfide is added to piperidine in water containing a surfactant. The reaction is shown as follows:

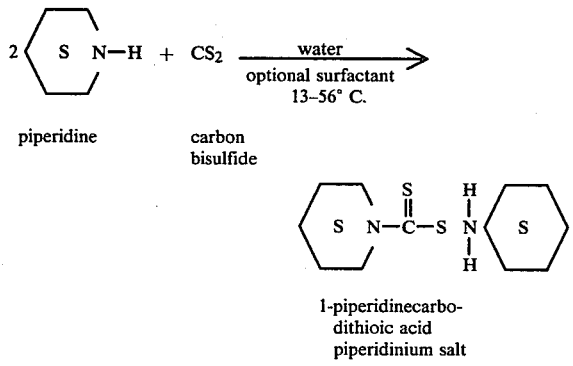

In addition to elimination of the fire hazard, there is the advantage of the prevention of pollution by ketone vapors emitted during the drying step. A further advantage of the process is the elimination of the step for the recovery of spent ketone.

DISCLOSURE OF THE INVENTION

In a specific embodiment of the invention, piperidine is added to water in an inert atmosphere. Distilled water is preferred to minimize contamination of the product. Filtrate water from the reaction can be recycled and used as solvent to optimize the yield. An inert atmosphere is used as a safety precaution. The process can be run at atmospheric pressure. The concentration of piperidine in the water may be generally 25 to 45% by weight. Preferably the concentration of piperidine is 40 to 45% by weight in the water. Concentrations below 25% by weight are uneconomical while concentrations above 45% by weight are inefficient. If the concentration is too low, too much product proportionately will be lost by solubility in water. If the concentration is higher than 45%, then it is difficult to stir and transfer. There will be a 10° C. heat rise on adding the piperidine.

Carbon bisulfide is then added to the solution at a temperature of 13°–27° C. The reaction of piperidine and carbon bisulfide is also exothermic. The temperature will rise at least 15° C. The solution is stirred at 13°–27° C. for 15 minutes. To stir longer than 15 minutes is not harmful, but will extend the time cycle unnecessarily. At these temperatures, the reaction is incomplete because some of the carbon bisulfide is absorbed on the surface of the 1-piperidine-carbodithioic acid piperidinium salt and does not react with the piperidine. At this point, the reaction solution is heated to above the boiling point of carbon bisulfide, preferably 52°–56° C. over 1–2 hours and held at 52°–56° C. for ½ hour. To hold the solution at this temperature range for up to one hour is not harmful but will extend the time cycle unnecessarily. At these temperatures, the vapors of carbon bisulfide leave the surface of the 1-piperidine-carbodithioic acid piperidine salt particles in suspension. As the carbon bisulfide vapors pass through the water solution of piperidine, they react with the remaining piperidine and the reaction is completed.

The solution is cooled to 0°–5° C. and held for 15 minutes. The product is filtered and washed at 0°–5° C. As the product is soluble in water, excess water should not be used in the wash because product will be lost in the filtrate. Filtrate water can be recycled and used as solvent for the next charge. The filter cake is dried at 60°–65° C. until the product contains less than 1% water.

In an optional process for preparing 1-piperidine-carbodithioic acid piperidinium salt, a surfactant is added to solvent water. The surfactant facilitates the reaction between ingredients piperidine and carbon bisulfide. In the practice of this invention, nonionic surfactants are used such as alcohol or organic phosphate condensation products of ethylene or propylene oxides. Examples of preferred surfactants are an ethylene oxide adduct of n-octyl phosphate and an ethylene oxide and propylene oxide adduct of tridecyl alcohol. From 0.1 to 1% by weight of surfactant based on the weight of piperidine should be present in the solvent water at the beginning of the reaction. Too much surfactant is uneconomical.

Piperidine is added to the aqueous solution in an inert atmosphere and there is a heat rise. An equivalent weight of carbon bisulfide is added to the solution at a temperature of 13°–27° C. The reaction of piperidine and carbon bisulfide is exothermic. The solution is stirred at 13°–27° C. for 15 minutes. To stir longer than 15 minutes is not harmful but will extend the time cycle unnecessarily. The surfactant attracts unreacted carbon bisulfide from the surface of 1-piperidine-carbodithioic acid piperidinium salt into the water phase where the carbon bisulfide reacts with the piperidine to complete the reaction. The mixture is heated to 35°–40° C. and held for 3 hours and then heated to 52°–56° C. and held for 15 minutes to insure that the carbon bisulfide has reacted completely. When this mixture is heated to 52°–56° C., the exotherm is no longer detected.

The solution is cooled to 0°–5° C. and held for 15 minutes. An excess of piperidine should be present. If a sample of the reaction product is checked on phenophthalein test paper, the paper should turn pink indicating the presence of excess piperidine. If the test paper remains colorless, add piperidine and agitate for 15 minutes. The reaction product 1-piperidine-carbodithioic acid piperidinium salt is filtered and washed with water that has been cooled to 0°-5° C. As the product is soluble in water, excess water should not be used in the wash because product will be lost in the filtrate. The filtrate can be recycled and used as the solvent for the next charge. The filter cake is dried at 60°-65° C. until the product contains less than 1% water.

The following examples further illustrate the process of the present invention.

EXAMPLE 1 (Water)

While maintaining a slow nitrogen purge, an enamel-lined reaction kettle was charged with 1,900 pounds of water. In an inert atmosphere 625 pounds of piperidine were added to the kettle. Agitation was begun and brine applied to the jacket. 276 Pounds of carbon bisulfide were added at a temperature between 13° and 27° C. and stirred for 15 minutes. The mixture was heated to 53°-56° C. over 1-2 hours. An exotherm raised the temperature to 65° C. The mixture was cooled to 0°-5° C., held for 15 minutes and filtered. Water was added to the kettle and cooled to 0°-5° C. The nutsch cake was washed with the cold water and dried in a steam-heated air drier at 60°-65° C. until the product contained less than 1% water. The yield was 669 pounds of dry 1-piperidine-carbodithioic acid piperidinium salt.

EXAMPLE 2 (Surfactant)

While maintaining a slow nitrogen purge, an enamel-lined reaction kettle was charged with 1,500 pounds of water and 1 pound of a surfactant consisting of ethylene oxide adduct of n-octyl phosphate. In an inert atmosphere 625 pounds of piperidine were added to the kettle. Agitation was begun and brine applied to the jacket. 276 Pounds of carbon bisulfide were added at a temperature between 13° and 27° C. and stirred for 15 minutes. The mixture was heated to 35°-40° C., held for 3 hours, heated to 52°-56° C., held for 15 minutes and then cooled to 0°-5° C. and held for 15 minutes. The mixture was then filtered on a nutsch. 150 Pounds of water was added to the kettle and cooled to 0°-5° C. The nutsch cake was washed with the cold water and dried in a steam-heated air drier at 60°-65° C. until the product contained less than 1% water. The yield was 796 pounds of dry 1-piperidine-carbodithioic acid piperidinium salt.

The following four experiments show that the filtrate from a charge can be used as the solvent for the next charge to optimize the yield.

EXAMPLE 3 (Surfactant)

0.1 cc of a surfactant containing an ethylene oxide adduct of n-octyl phosphate and 62.5 g of piperidine were added to 150 ml of deionized water. 27.6 g of carbon bisulfide were added while maintaining a temperature of 13°-27° C. and the mixture was held in that temperature range for ¼ hour. The mixture was then heated to 35°-40° C., held for 3 hours, heated to 52°-56° C., held for ¼ hour, cooled to 0°-5° C., held for ¼ hour and filtered. The filter cake was washed with 15 ml of deionized water at 0°-5° C. The cake was dried. Yield was 79.6 g, filtrate was 159 ml.

EXAMPLE 4

Example 3 was repeated except the 159 ml of filtrate were used as solvent instead of 150 ml of deionized water. Yield was 86.2 g, filtrate was 161 ml.

EXAMPLE 5

Example 3 was repeated except 161 ml of filtrate were used as solvent instead of fresh water. The yield was 87.2 g, filtrate was 162 ml.

EXAMPLE 6

Example 3 was repeated except 162 ml of filtrate were used as solvent instead of 150 ml of fresh water. Yield was 87.7 g, filtrate was 162 ml.

The following two experiments show that a surfactant is needed to maintain fluidity when the concentration of product is high and a minimum of water is used.

EXAMPLE 7

0.2 cc of a surfactant containing an ethylene oxide and propylene oxide adduct of tridecyl alcohol and 125 g of piperidine were added to 150 ml of deionized water. 56.4 g of carbon bisulfide were added while the mixture was maintained at 13°-27° C. The mixture was stirred for ¼ hour at 13°-27° C., heated to 52°-56° C., held 2½ hours, cooled to 0°-5° C., held ¼ hour and filtered. The filter cake was washed with 30 ml of deionized water at 0°-5° C. The cake was dried. Yield was 169.3 g.

EXAMPLE 8

125 g of piperidine was added to 150 ml of deionized water. 56.4 g of carbon bisulfide were added while maintaining a temperature of 13°-27° C. A ball of solids formed which slowly stirred in. The mixture was stirred for ¼ hour at 13°-27° C. and heated to 52°-56° C. At 52°-56° C. the mixture became a solid mass which stopped the agitator.

I claim:

1. A process for preparing 1-piperidine-carbodithioic acid piperidinium salt comprising reacting piperidine in water with carbon bisulfide. and heating to 52°-56° C.

2. A process for preparing 1piperidine-carbodithioic acid piperidinium salt comprising reacting piperidine in water containing a surfactant with carbon bisulfide and heating to 52°-56° C.

3. A process of claim 2 wherein the surfactant is an ethylene oxide adduct of n-octyl phosphate.

4. A process of claim 2 wherein the surfactant is an ethylene oxide and propylene oxide adduct of tridecyl alcohol.

5. A process for preparing 1-piperidine-carbodithioic acid piperidinium salt comprising reacting piperidine in water, optionally containing a surfactant, and carbon bisulfide at a temperature of 13°-27° C., then heating the solution above the boiling point of carbon bisulfide until the reaction is completed.

6. The process of claim 5 wherein the solution is heated to 52°-56° C. until the reaction is completed.

* * * * *